(12) United States Patent
Gordon et al.

(10) Patent No.: US 8,414,605 B2
(45) Date of Patent: Apr. 9, 2013

(54) VACUUM LEVEL CONTROL OF POWER FOR PHACOEMULSIFICATION HAND PIECE

(75) Inventors: Raphael Gordon, Ladera Ranch, CA (US); Ahmad Salehi, Irvine, CA (US); Dan Teodorescu, Fountain Valley, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 95 days.

(21) Appl. No.: 13/178,845

(22) Filed: Jul. 8, 2011

(65) Prior Publication Data
US 2013/0012868 A1    Jan. 10, 2013

(51) Int. Cl.
*A61B 17/32* (2006.01)
(52) U.S. Cl.
USPC ........................................................ 606/169
(58) Field of Classification Search ................... 606/107, 606/166, 167, 169, 170, 171, 180; 604/22
See application file for complete search history.

(56) References Cited

U.S. PATENT DOCUMENTS

| | | | |
|---|---|---|---|
| 3,526,219 A | 9/1970 | Balamuth |
| 3,589,363 A | 6/1971 | Banko et al. |
| 3,601,126 A | 8/1971 | Estes |
| 3,693,613 A | 9/1972 | Kelman |
| 3,812,855 A | 5/1974 | Banko |
| 3,812,858 A | 5/1974 | Oringer |
| 3,857,387 A | 12/1974 | Shock |
| 3,902,495 A | 9/1975 | Weiss et al. |
| 3,930,505 A | 1/1976 | Wallach |
| 3,942,519 A | 3/1976 | Shock |
| 3,952,732 A | 4/1976 | Shock |
| 3,956,826 A | 5/1976 | Perdreaux, Jr. |
| 3,964,487 A | 6/1976 | Judson |
| 3,990,452 A | 11/1976 | Murry et al. |
| 4,024,467 A | 5/1977 | Andrews et al. |
| 4,024,866 A | 5/1977 | Wallach |
| 4,114,623 A | 9/1978 | Meinke et al. |
| 4,126,137 A | 11/1978 | Archibald |

(Continued)

FOREIGN PATENT DOCUMENTS

| | | |
|---|---|---|
| EP | 359217 | 3/1990 |
| EP | 0359217 A2 | 3/1990 |

(Continued)

OTHER PUBLICATIONS

Shuyu, Lin. "Sandwiched Piezoelectric Ultrasonic Transducers of Longitudinal-Torsional Compound Vibrational Modes." IEEE Transactions of Ultrasonics, Ferroelectrics and Frequency Control, Nov. 1997, pp. 1189-1197.

(Continued)

*Primary Examiner* — Ryan Severson
*Assistant Examiner* — Jonathan W Miles
(74) *Attorney, Agent, or Firm* — Kenneth Bassinger

(57) ABSTRACT

The present invention comprises a method of operating an ophthalmic surgical hand piece, providing a series of power pulses to the hand piece, each of the series of power pulses having a first portion that produces torsional movement of a cutting tip and a second portion that produces longitudinal movement of the cutting tip; measuring vacuum pressure; altering the duration of the first portion as vacuum pressure increases; and altering the duration of the second portion as vacuum pressure increases.

10 Claims, 4 Drawing Sheets

U.S. PATENT DOCUMENTS

| | | |
|---|---|---|
| 4,156,187 A | 5/1979 | Murry et al. |
| 4,168,707 A | 9/1979 | Douvas et al. |
| 4,184,510 A | 1/1980 | Murry et al. |
| 4,223,676 A | 9/1980 | Wuchinich et al. |
| 4,246,902 A | 1/1981 | Martinez |
| 4,248,232 A | 2/1981 | Engelbrecht et al. |
| 4,406,284 A | 9/1983 | Banko |
| 4,417,578 A | 11/1983 | Banko |
| 4,493,694 A | 1/1985 | Wuchinich et al. |
| 4,496,342 A | 1/1985 | Banko |
| 4,504,264 A | 3/1985 | Kelman |
| 4,508,532 A | 4/1985 | Drews et al. |
| 4,515,583 A | 5/1985 | Sorich |
| 4,589,415 A | 5/1986 | Haaga |
| 4,590,935 A | 5/1986 | Ranalli |
| 4,609,368 A | 9/1986 | Dotson, Jr. |
| 4,651,280 A | 3/1987 | Chang et al. |
| 4,658,819 A | 4/1987 | Harris et al. |
| 4,705,500 A | 11/1987 | Reimels et al. |
| 4,712,544 A | 12/1987 | Ensslin |
| 4,739,759 A | 4/1988 | Rexroth et al. |
| 4,750,488 A | 6/1988 | Wuchinich et al. |
| 4,770,654 A | 9/1988 | Rogers et al. |
| 4,793,346 A | 12/1988 | Mindich |
| 4,827,911 A | 5/1989 | Broadwin et al. |
| 4,869,715 A | 9/1989 | Sherburne |
| 4,922,902 A | 5/1990 | Wuchinich et al. |
| 4,961,424 A | 10/1990 | Kubota et al. |
| 4,969,885 A | 11/1990 | Farin |
| 4,989,588 A | 2/1991 | Kubota et al. |
| 5,026,387 A | 6/1991 | Thomas |
| 5,116,343 A | 5/1992 | Ames et al. |
| 5,139,509 A | 8/1992 | Fischer et al. |
| 5,151,085 A | 9/1992 | Sakurai et al. |
| 5,154,694 A | 10/1992 | Kelman |
| 5,154,696 A | 10/1992 | Shearing |
| 5,160,317 A | 11/1992 | Costin |
| 5,180,363 A | 1/1993 | Idemoto et al. |
| 5,188,102 A | 2/1993 | Idemoto et al. |
| 5,188,589 A | 2/1993 | Wypych et al. |
| 5,205,817 A | 4/1993 | Idemoto et al. |
| 5,242,385 A | 9/1993 | Strukel |
| 5,279,547 A | 1/1994 | Costin |
| 5,304,115 A | 4/1994 | Pflueger et al. |
| 5,331,951 A | 7/1994 | Kepley |
| 5,342,293 A | 8/1994 | Zanger |
| 5,359,996 A | 11/1994 | Hood |
| 5,431,664 A | 7/1995 | Ureche et al. |
| 5,520,633 A | 5/1996 | Costin |
| 5,569,188 A | 10/1996 | Mackool |
| 5,591,127 A | 1/1997 | Barwick, Jr. et al. |
| 5,676,649 A | 10/1997 | Boukhny et al. |
| 5,700,240 A | 12/1997 | Barwick, Jr. et al. |
| 5,722,945 A | 3/1998 | Anis et al. |
| 5,733,256 A | 3/1998 | Costin |
| 5,766,146 A | 6/1998 | Barwick, Jr. |
| 5,808,396 A | 9/1998 | Boukhny |
| 5,865,790 A | 2/1999 | Bair |
| 5,938,677 A | 8/1999 | Boukhny et al. |
| 6,027,515 A | 2/2000 | Cimino |
| 6,028,387 A | 2/2000 | Boukhny |
| 6,077,285 A | 6/2000 | Boukhny |
| 6,083,193 A | 7/2000 | Kadziauskas et al. |
| 6,165,190 A * | 12/2000 | Nguyen .................. 606/166 |
| 6,175,180 B1 | 1/2001 | Angelini et al. |
| 6,179,805 B1 | 1/2001 | Sussman et al. |
| 6,179,808 B1 | 1/2001 | Boukhny et al. |
| 6,193,683 B1 | 2/2001 | Ludin et al. |
| 6,241,700 B1 | 6/2001 | Leukanech |
| 6,258,111 B1 * | 7/2001 | Ross et al. .................. 606/171 |
| 6,261,283 B1 | 7/2001 | Morgan et al. |
| 6,261,297 B1 | 7/2001 | Kadziauskas et al. |
| 6,283,974 B1 | 9/2001 | Alexander |
| 6,315,755 B1 | 11/2001 | Sussman |
| 6,402,769 B1 | 6/2002 | Boukhny |
| 6,491,661 B1 | 12/2002 | Boukhny et al. |
| 6,506,176 B1 * | 1/2003 | Mittelstein et al. ............. 604/22 |
| 6,629,948 B2 | 10/2003 | Rockley |
| 6,679,899 B2 | 1/2004 | Wiener et al. |
| 6,699,212 B1 | 3/2004 | Kadziauskas |
| 6,780,165 B2 | 8/2004 | Kadziauskas et al. |
| 7,229,455 B2 | 6/2007 | Sakurai et al. |
| 7,297,137 B2 | 11/2007 | Gordon et al. |
| 7,316,664 B2 | 1/2008 | Kadziauskas et al. |
| 7,374,552 B2 * | 5/2008 | Wuchinich ............. 604/22 |
| 7,485,106 B2 | 2/2009 | Kadziauskas et al. |
| 7,572,242 B2 * | 8/2009 | Boukhny .................. 604/22 |
| 7,645,255 B2 | 1/2010 | Gordon et al. |
| 7,651,490 B2 * | 1/2010 | Boukhny et al. .................. 606/1 |
| 7,758,538 B2 | 7/2010 | Boukhny et al. |
| 8,016,843 B2 * | 9/2011 | Escaf ............. 606/166 |
| 2001/0001123 A1 | 5/2001 | Madan et al. |
| 2001/0011176 A1 | 8/2001 | Boukhny |
| 2003/0045887 A1 | 3/2003 | Sakurai et al. |
| 2004/0092800 A1 * | 5/2004 | MacKool ............. 600/300 |
| 2004/0092922 A1 | 5/2004 | Kadziauskas et al. |
| 2005/0209621 A1 * | 9/2005 | Gordon et al. ............. 606/169 |
| 2005/0261628 A1 * | 11/2005 | Boukhny et al. ............. 604/118 |
| 2005/0261715 A1 * | 11/2005 | Boukhny et al. ............. 606/169 |
| 2005/0267504 A1 * | 12/2005 | Boukhny et al. ............. 606/171 |
| 2005/0277869 A1 * | 12/2005 | Boukhny ............. 604/22 |
| 2006/0041200 A1 | 2/2006 | Dotter et al. |
| 2006/0079788 A1 | 4/2006 | Anderson et al. |
| 2008/0146989 A1 * | 6/2008 | Zacharias ............. 604/22 |
| 2009/0082715 A1 * | 3/2009 | Charles ............. 604/22 |
| 2010/0152761 A1 * | 6/2010 | Mark ............. 606/180 |
| 2010/0324581 A1 * | 12/2010 | Mackool et al. ............. 606/169 |

FOREIGN PATENT DOCUMENTS

| | | |
|---|---|---|
| EP | 1729658 | 12/2006 |
| EP | 1765190 | 3/2007 |
| EP | 1990032 A1 | 11/2008 |
| EP | 1990032 B1 | 3/2010 |
| WO | WO 87/05793 | 10/1987 |
| WO | WO 92/07622 | 5/1992 |
| WO | WO 95/20374 | 8/1995 |
| WO | WO 99/18901 | 4/1999 |
| WO | WO 99/45868 | 9/1999 |
| WO | WO 01/24744 | 4/2001 |
| WO | WO 01/41672 A2 | 6/2001 |
| WO | WO 01/97728 | 12/2001 |
| WO | WO 02/17833 | 3/2002 |
| WO | WO 02/056806 | 7/2002 |
| WO | WO 03/043550 | 5/2003 |
| WO | WO 2004/080505 A2 | 9/2004 |
| WO | WO 2010/014937 A1 | 2/2010 |

OTHER PUBLICATIONS

Jiromaru Tsujino, "Ultrasonic Motor Using a One-Dimensional Longitudinal-Torsional Vibration Converter With Diagonal Slits", Smart Mater. Struct. 7 (1998) 345-351.

International Searching Authority, Written Opinion of the International Searching Authority, PCT/US2012/044807, Sep. 27, 2012, 5 pages.

International Searching Authority, Declaration of Non-Establishment of International Search Report, PCT/US2012/044807, Sep. 27, 2012, 2 pages.

* cited by examiner

☐ Torsional   ■ Longitudinal   ▨ Longitudinal + Torsional

VACUUM LEVEL CONTROL OF POWER FOR PHACOEMULSIFICATION HAND PIECE

BACKGROUND OF THE INVENTION

The present invention relates to phacoemulsification surgery and more particularly to the control of a phacoemulsification hand piece that is capable of imparting both longitudinal and torsional motion to a cutting tip.

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. A typical surgical hand piece suitable for phacoemulsification procedures consists of an ultrasonically driven phacoemulsification hand piece, an attached hollow cutting needle surrounded by an irrigating sleeve, and an electronic control console. The hand piece assembly is attached to the control console by an electric cable and flexible tubing. Through the electric cable, the console varies the power level transmitted by the hand piece to the attached cutting needle. The flexible tubing supplies irrigation fluid to the surgical site and draws aspiration fluid from the eye through the hand piece assembly.

The operative part in a typical hand piece is a centrally located, hollow resonating bar or horn directly attached to a set of piezoelectric crystals. The crystals supply the required ultrasonic vibration needed to drive both the horn and the attached cutting needle during phacoemulsification, and are controlled by the console. The crystal/horn assembly is suspended within the hollow body or shell of the hand piece by flexible mountings. The hand piece body terminates in a reduced diameter portion or nosecone at the body's distal end. Typically, the nosecone is externally threaded to accept the hollow irrigation sleeve, which surrounds most of the length of the cutting needle. Likewise, the horn bore is internally threaded at its distal end to receive the external threads of the cutting tip. The irrigation sleeve also has an internally threaded bore that is screwed onto the external threads of the nosecone. The cutting needle is adjusted so that its tip projects only a predetermined amount past the open end of the irrigating sleeve.

During the phacoemulsification procedure, the tip of the cutting needle and the end of the irrigation sleeve are inserted into the anterior capsule of the eye through a small incision in the outer tissue of the eye. The surgeon brings the tip of the cutting needle into contact with the lens of the eye, so that the vibrating tip fragments the lens. The resulting fragments are aspirated out of the eye through the interior bore of the cutting needle, along with irrigation solution provided to the eye during the procedure, and into a waste reservoir.

Power is applied to the hand piece to vibrate the cutting needle. In general, the amplitude of needle movement (or vibration) is proportional to the power applied. In conventional phacoemulsification systems, the needle vibrates back and forth producing a longitudinal needle stroke. In improved systems, the needle may be caused to vibrate in a twisting or torsional motion. One way to achieve twisting or torsional motion is described in U.S. Pat. No. 7,651,490. Twisting or torsional motion of the cutting tip has proven a very effective way of removing lens material. Twisting or torsional movement of the cutting tip avoids repulsion that can occur with traditional longitudinal movement of the cutting tip and leads to more effective lens removal. In some cases, however, because torsional or twisting motion of the cutting tip prevents repulsion of lens material, such motion induces a clogging or occlusion of the cutting tip. Longitudinal motion may be used to clear an occluded tip by pushing the lens material away from the tip. As such, during cataract surgery both longitudinal and torsional or twisting motion may be desirable depending on the circumstances. Moreover, it may also be desirable to control of the type of motion based on an occluded state of the cutting tip.

SUMMARY OF THE INVENTION

In one embodiment consistent with the principles of the present invention, the present invention comprises a method of operating an ophthalmic surgical hand piece, providing a series of power pulses to the hand piece, each of the series of power pulses having a first portion that produces torsional movement of a cutting tip and a second portion that produces longitudinal movement of the cutting tip; measuring vacuum pressure; altering the duration of the first portion as vacuum pressure increases; and altering the duration of the second portion as vacuum pressure increases.

In another embodiment consistent with the principles of the present invention, the present invention comprises a method of operating an ophthalmic surgical hand piece, providing a series of power pulses to the hand piece, each of the series of power pulses having a first portion that produces torsional movement of a cutting tip and a second portion that produces simultaneous torsional and longitudinal movement of the cutting tip; measuring vacuum pressure; altering the duration of the first portion as vacuum pressure increases; and altering the duration of the second portion as vacuum pressure increases.

In another embodiment consistent with the principles of the present invention, the present invention comprises a method of operating an ophthalmic surgical hand piece, providing a series of power pulses to the hand piece, each of the series of power pulses having a first portion that produces torsional movement of a cutting tip, a second portion that produces simultaneous torsional and longitudinal movement of the cutting tip, and a third portion that produces longitudinal movement of the cutting tip; measuring vacuum pressure; altering the duration of the first portion as vacuum pressure increases; altering the duration of the second portion as vacuum pressure increases; and altering the duration of the third portion as vacuum pressure increases.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
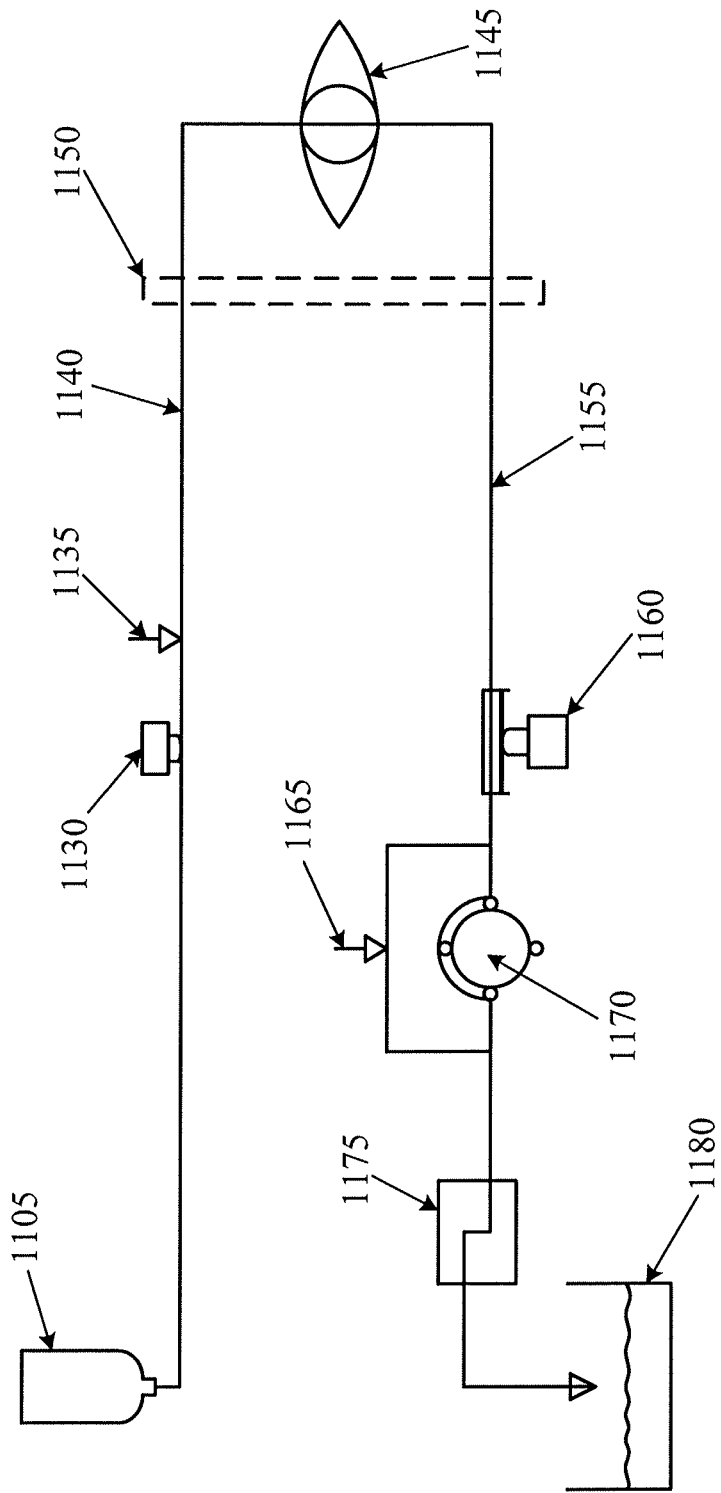
FIG. 1 is a diagram of the components in the fluid path of a phacoemulsification system.

In one embodiment of the present invention, FIG. 1 is a diagram of the components in the fluid path of a phacoemulsification system. FIG. 1 depicts the fluid path through the eye 1145 during cataract surgery. The components include an irrigation fluid source 1105, an irrigation pressure sensor 1130, an irrigation valve 1135, an irrigation line 1140, a hand piece 1150, an aspiration line 1155, an aspiration pressure sensor 1160, a vent valve 1165, a pump 1170, a reservoir 1175 and a drain bag 1180. The irrigation line 1140 provides irrigation fluid to the eye 1145 during cataract surgery. The aspiration line 1155 removes fluid and emulsified lens particles from the eye during cataract surgery.

When irrigation fluid exits irrigation fluid source 1105, it travels through irrigation line 1140 and into the eye 1145. An irrigation pressure sensor 1130 measures the pressure of the irrigation fluid in irrigation line 1140. An optional irrigation valve 1135 is also provided for on/off control of irrigation. Irrigation pressure sensor 1130 is implemented by any of a number of commercially available fluid pressure sensors and can be located anywhere in the irrigation fluid path (anywhere between the irrigation source 1105 and the eye 1145).

A hand piece 1150 is placed in the eye 1145 during a phacoemulsification procedure. The hand piece 1150 has a hollow needle (as seen in FIG. 2) that is ultrasonically vibrated in the eye to break up the diseased lens. A sleeve located around the needle provides irrigation fluid from irrigation line 1140. The irrigation fluid passes through the space between the outside of the needle and the inside of the sleeve (as more clearly shown in FIG. 2A). Fluid and lens particles are aspirated through the hollow needle. In this manner, the interior passage of the hollow needle is fluidly coupled to aspiration line 1155. Pump 1170 draws the aspirated fluid from the eye 1145. An aspiration pressure sensor 1160 measures the pressure in the aspiration line. An optional vent valve can be used to vent the vacuum created by pump 1170. The aspirated fluid passes through reservoir 1175 and into drain bag 1180.

When the hollow needle is wholly or partially occluded with a lens particle (an "occlusion"), aspiration pressure sensor 1160 detects an increase in vacuum pressure in aspiration line 1155. Because the pump 1170 continues to run during the surgical procedure to remove the diseased lens, when an occlusion occurs, vacuum pressure increases in aspiration line 1155 up to a vacuum limit (the vacuum limit depends on the pump 1170). The vacuum limit achievable by pump 1170 is generally the maximum vacuum level that the pump 1170 can produce in the system. In normal operation, the pump 1170 will be shut off before the vacuum limit is reached.

When the hollow needle is not occluded, pump 1170 operates to produce a relatively constant vacuum pressure in aspiration line 1155. The difference between this "normal" vacuum pressure and the vacuum limit can be very significant. An occlusion is generally a transitory event that lasts on average a few seconds—the lens particle that occludes the hollow needle is eventually broken up and aspirated out of the eye (an "occlusion break"). When an occlusion break occurs, vacuum pressure in the aspiration line 1155 (and the eye as well) decreases rapidly as fluid and lens particles are aspirated from the eye. This pressure fluctuation is not desirable as it can lead to collapse of the anterior chamber of the eye.

The aspiration pressure sensor 1160 and the irrigation pressure sensor 1130 can detect an increase in pressure related to an occlusion and a decrease in pressure associated with occlusion break. The increase in pressure associated with an occlusion is gradual in that it increases over a few seconds. The decrease in pressure associated with an occlusion break is much more rapid. When the pressure measured by the irrigation pressure sensor 1130 or the aspiration pressure sensor 1160 increases, an occlusion is likely to have occurred. The measured pressure increases gradually over a few seconds to a vacuum setting that may or may not be at the vacuum limit. When this vacuum setting is reached, the pump 1170 is turned off to prevent further increase in pressure.

Figure 2A:
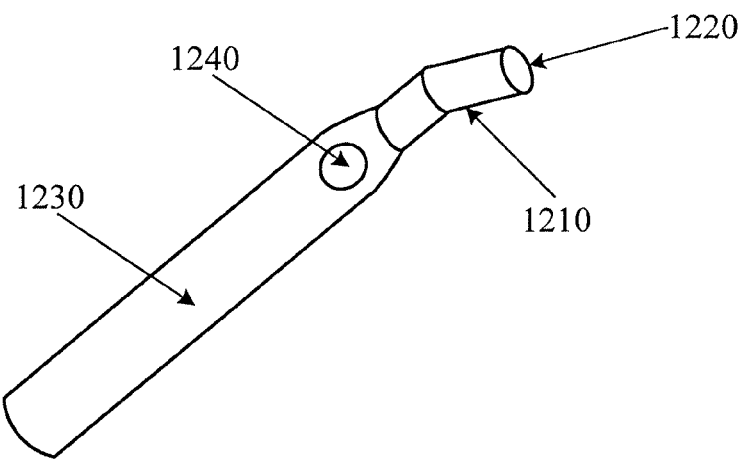
FIGS. 2A-2D are perspective views of the distal end of a phacoemulsification needle and irrigation sleeve according to the principles of the present invention.
Figure 2B:
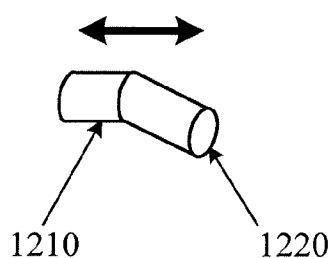
Figure 2C:
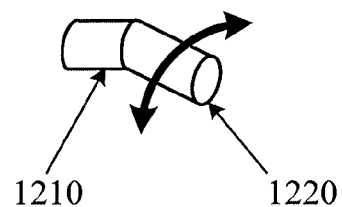
Figure 2D:
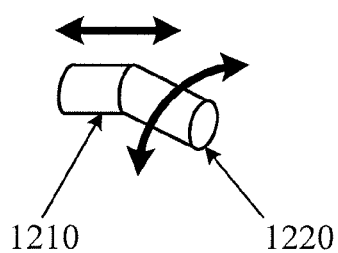

FIG. 2A is a perspective view of the distal end of a phacoemulsification hand piece according to the principles of the present invention. In FIG. 2, a phacoemulsification needle 1210 is surrounded by an irrigation sleeve 1230. The phacoemulsification needle 1210 has an open end 1220 through which lens particles are aspirated from the eye during cataract surgery. The irrigation sleeve 1230 has an optional opening 1240 through which irrigation fluid flows into the eye. The needle 1210 and sleeve 1230 are both inserted into the anterior chamber of the eye during cataract surgery. When power is applied to the hand piece, the needle 1210 vibrates ultrasonically in a longitudinal mode, a torsional mode, or in both modes simultaneously. This is more clearly seen in FIGS. 2B-2D. In FIG. 2B, needle 1210 vibrates in longitudinal mode (back and forth). In FIG. 2C, needle 1210 vibrates in torsional mode (or in a twisting or sweeping manner). In FIG. 2D, needle 1210 vibrates in both longitudinal and torsional modes simultaneously.

The two different modes (longitudinal and torsional) produce two different needle motions as shown in FIGS. 2B-2D. In general, longitudinal mode can act to cut a cataractous lens by impacting the end of the needle 1210 against the lens much like a jackhammer. Torsional mode can act to cut a lens with a side to side sweep of the end of the needle 1210. Depending on the needle geometry, the twisting motion imparted to the needle 1210 in torsional mode generally produces a side to side sweep of the end of the needle 1210. In other instances, the end of the needle 1210 sweeps in an arc. Regardless, torsional mode may be more effective in cutting a lens because it allows aspiration through open end 1220 of needle 1210 to hold the lens material on the needle 1210 for more effective cutting. In addition, in torsional mode, each sweep of the needle 1210 acts to cut the lens. In contrast, longitudinal mode produces a jack hammer motion that impacts the lens only in a forward direction (and not in a return direction). Moreover, longitudinal mode may act to repel the lens material away from the needle which may reduce cutting efficiency. However, when the open end 1220 of the needle 1210 is occluded or blocked by lens material, the repulsion effect of longitudinal mode may be effective at clearing the material which can be desirable.

When both modes are operated simultaneously, the needle 1210 moves both longitudinally and torsionally at the same time. The amount of longitudinal and torsional motion can be controlled independently as explained below. In some instances, this combination motion may be more effective at cutting the lens and/or clearing lens material from the open end 1220 of needle 1210.

Figure 3:
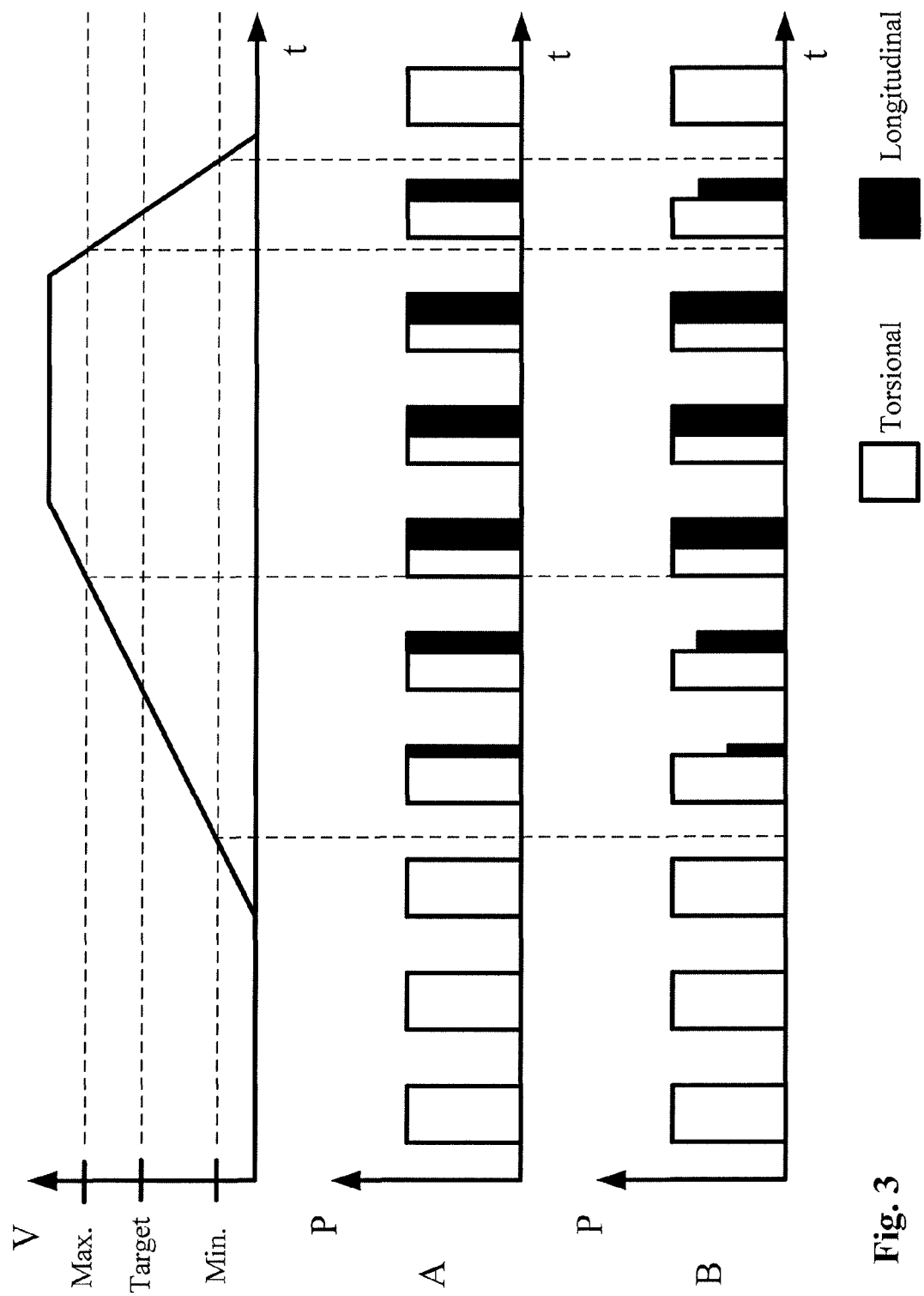
FIG. 3 is a diagram of a mode of controlling power in response to vacuum level according to the principles of the present invention.

FIG. 3 is a diagram of a mode of controlling power in response to vacuum pressure according to the principles of the present invention. The first plot in FIG. 3 represents vacuum pressure (V) over time. The second plot in FIG. 3 (plot A) represents one mode of controlling power (P) in response to vacuum (V) in the first plot. The third plot in FIG. 3 (plot B) represents a second mode of controlling power (P) in response to vacuum (V) in the first plot.

The first plot represents an occlusion and occlusion break. As noted with respect to FIG. 1, vacuum pressure increases over time when an occlusion occurs until a vacuum setting is reached. Upon occlusion break, vacuum pressure decreases rapidly. In FIG. 3, the target vacuum (designated by "Target") is a vacuum setting that may be selected by an operator of the phacoemulsification console or may be pre-programmed. The target vacuum is a vacuum pressure selected from the range of possible vacuum pressures that can be created by pump 1170. A vacuum pressure range is established from the target vacuum (the range from Min. to Max. as seen on the first plot in FIG. 3). The Min. vacuum may be a fraction of the target vacuum, while the Max. vacuum may be a multiple of the target vacuum. For example, the Min. vacuum may be 75% of the target vacuum, while the Max. vacuum may be 125% of the target vacuum. However, any percentages, fractions or multiples may be used to calculate Min. vacuum and Max. vacuum.

Plot A of FIG. 3 shows one mode of controlling power applied to a phacoemulsification hand piece in response to a vacuum pressure. Plot A shows the application of power in pulse mode. In pulse mode, power to the hand piece is pulsed. In pulse mode, each pulse has an amplitude, an on time, and an off time (of zero power as shown, but alternatively of a reduced power level). In this manner, pulse mode can be characterized by an amplitude of pulses and a duty cycle of pulses. The white pulses (or white portions of pulses) indicate torsional movement of the cutting tip—power is applied to the hand piece such that torsional movement of the cutting tip results. The black portion of the pulses indicates longitudinal movement of the cutting tip—power is applied to the hand piece such that longitudinal movement of the cutting tip results. In this manner, power is controlled to produce either torsional or longitudinal movement of the cutting tip.

As seen in plot A of FIG. 3, when the vacuum pressure is below Min. vacuum, each power pulses produces torsional movement of the cutting tip. As vacuum pressure increases from Min. vacuum to Max. vacuum, a first portion of the power pulse produces torsional movement of the cutting tip (denoted by the white area), and a second portion of the power pulse produces longitudinal movement of the cutting tip (denoted by the black area). As vacuum pressure increases, a greater portion of the power pulse produces longitudinal movement of the cutting tip. Recall that longitudinal movement of the cutting tip can be used to clear an occlusion. Therefore, as vacuum pressure increases (which indicates an occlusion is present), greater periods of longitudinal movement are applied to the cutting tip in an attempt to clear the occlusion. As the duration of the occlusion increases (and the vacuum pressure increases), more longitudinal movement is imparted to the cutting tip during each power pulse. This is seen in the fourth, fifth, and sixth power pulses in plot A. For example, the amount of longitudinal movement can be proportional to the vacuum pressure.

When the vacuum pressure exceeds the Max. vacuum, each power pulse produces approximately equal amounts of torsional and longitudinal movement at the cutting tip. Alternatively, the amount of longitudinal movement can be increased to any desired level (e.g. 25% torsional, 75% longitudinal; 10% torsional, 90% longitudinal, 0% torsional, 100% longitudinal). While plot A shows that torsional movement is followed by longitudinal movement, the power pulses can be such that longitudinal movement is followed by torsional movement. Further, the duration of each type of power pulse (torsional and longitudinal) can be set to any desired period.

Plot B is similar to plot A except that both the amplitude and duration of the longitudinal pulse is controlled in response to vacuum level. Plot B shows the application of power in pulse mode. In pulse mode, power to the hand piece is pulsed. In pulse mode, each pulse has an amplitude, an on time, and an off time (of zero power as shown, but alternatively of a reduced power level). In this manner, pulse mode can be characterized by an amplitude of pulses and a duty cycle of pulses. The white pulses (or white portions of pulses) indicate torsional movement of the cutting tip—power is applied to the hand piece such that torsional movement of the cutting tip results. The black portion of the pulses indicates longitudinal movement of the cutting tip—power is applied to the hand piece such that longitudinal movement of the cutting tip results. In this manner, power is controlled to produce either torsional or longitudinal movement of the cutting tip.

As seen in plot B of FIG. 3, when the vacuum pressure is below Min. vacuum, each power pulses produces torsional movement of the cutting tip. As vacuum pressure increases from Min. vacuum to Max. vacuum, a first portion of the power pulse produces torsional movement of the cutting tip (denoted by the white area), and a second portion of the power pulse produces longitudinal movement of the cutting tip (denoted by the black area). The second portion of the pulse has an amplitude that is proportional to the vacuum level. In this case, as vacuum level increases from Min. vacuum to Max. vacuum, the amplitude of the pulse portion that produces longitudinal movement of the tip increases from a lower amplitude to a higher amplitude. In addition, as vacuum pressure increases, a greater portion of the power pulse produces longitudinal movement of the cutting tip. Recall that longitudinal movement of the cutting tip can be used to clear an occlusion. Therefore, as vacuum pressure increases (which indicates an occlusion is present), greater periods and amplitudes of longitudinal movement are applied to the cutting tip in an attempt to clear the occlusion. As the duration of the occlusion increases (and the vacuum pressure increases), more longitudinal movement is imparted to the cutting tip during each power pulse. This is seen in the fourth, fifth, and sixth power pulses in plot A. For example, the amount of longitudinal movement can be proportional to the vacuum pressure.

When the vacuum pressure exceeds the Max. vacuum, each power pulse produces approximately equal amounts of torsional and longitudinal movement at the cutting tip. Alternatively, the amount of longitudinal movement can be increased to any desired level (e.g. 25% torsional, 75% longitudinal; 10% torsional, 90% longitudinal, 0% torsional, 100% longitudinal). While plot A shows that torsional movement is followed by longitudinal movement, the power pulses can be such that longitudinal movement is followed by torsional movement. In additional, other variations of pulse amplitude may be employed. For example, the amplitude of the longitudinal portion of the power pulse may be less than, equal to, or greater than the amplitude of the torsional portion of the power pulse. Further, the duration of each type of power pulse (torsional and longitudinal) can be set to any desired period.

FIGS. 4A-4F are diagrams of power pulses according to the principles of the present invention. Any of these power pulses can be used in conjunction with or to replace the pulses in FIG. 3. In FIGS. 4A-4F, the white pulse (or the white portion of a pulse) represents torsional movement of the cutting tip—power is applied to the hand piece such that torsional movement of the cutting tip results. The black pulses (or black portion of the pulses) represents longitudinal movement of the cutting tip—power is applied to the hand piece such that longitudinal movement of the cutting tip results. The gray pulses (or gray portion of the pulses) represent a combination of longitudinal and torsional movement at the cutting tip—power is applied to the hand piece such that simultaneous longitudinal and torsional movement results at the cutting tip. In this manner, power is controlled to produce torsional, longitudinal, or simultaneous torsional and longitudinal movement of the cutting tip.

Figure 4A:
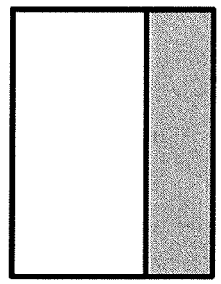
FIGS. 4A-4F are diagrams of power pulses according to the principles of the present invention.

FIG. 4A depicts a power pulse with a first portion that produces torsional movement of the cutting tip and a second portion that produces simultaneous torsional and longitudinal movement of the cutting tip. The duration of the simultaneous torsional and longitudinal movement of the cutting tip may be proportional to the vacuum pressure. As vacuum pressure increases, the duration of the pulse that produces torsional movement may decrease, while the duration of the pulse that produces simultaneous torsional and longitudinal motion may increase in a manner similar to that depicted in plot A of FIG. 3. In addition, the relative percentages of torsional and longitudinal movement can be further controlled such that the ratio of longitudinal movement to torsional movement (or the ratio of longitudinal power to torsional power) is varied. For example, the proportion of simultaneous torsional and longitudinal movement can be varied such that relatively more longitudinal movement (and relatively less torsional movement) is present at the cutting tip.

Figure 4B:
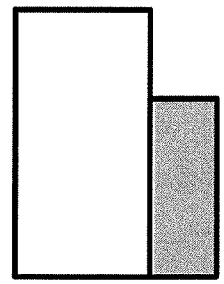

FIG. 4B depicts a power pulse with a first portion that produces torsional movement of the cutting tip and a second portion that produces simultaneous torsional and longitudinal movement of the cutting tip. The amplitude and duration of the simultaneous torsional and longitudinal movement of the cutting tip may be proportional to the vacuum pressure. As vacuum pressure increases, the amplitude and duration of the pulse that produces torsional movement may decrease, while the duration of the pulse that produces simultaneous torsional and longitudinal motion may increase in a manner similar to that depicted in plot B of FIG. 3. In addition, the relative percentages of torsional and longitudinal movement can be further controlled such that the ratio of longitudinal movement to torsional movement (or the ratio of longitudinal power to torsional power) is varied. For example, the proportion of simultaneous torsional and longitudinal movement can be varied such that relatively more longitudinal movement (and relatively less torsional movement) is present at the cutting tip.

Figure 4C:
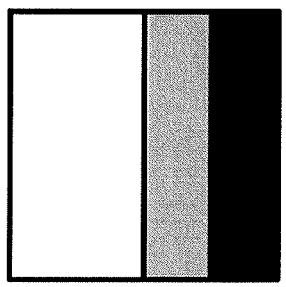

FIG. 4C depicts a power pulse with a first portion that produces torsional movement of the cutting tip, a second portion that produces simultaneous torsional and longitudinal movement of the cutting tip, and a third portion that produces longitudinal motion of the cutting tip. The duration of the simultaneous torsional and longitudinal movement of the cutting tip may be proportional to the vacuum pressure. As vacuum pressure increases, the duration of the pulse that produces torsional movement may decrease, while the duration of the pulse that produces simultaneous torsional and longitudinal motion may increase in a manner similar to that depicted in plot A of FIG. 3. Likewise, the duration of the longitudinal movement of the cutting tip may be proportional to the vacuum pressure. As vacuum pressure increases, the duration of the pulse that produces torsional movement may decrease, while the duration of the pulse that produces longitudinal motion may increase in a manner similar to that depicted in plot A of FIG. 3. In another embodiment of the present invention, the portion of the pulse that produces torsional movement of the cutting tip may be decreased as vacuum pressure increases, while the remaining portion of the power pulse may include a first portion that produces simultaneous torsional and longitudinal movement of the cutting tip and a second portion that produces longitudinal movement of the cutting tip. The first and second portions may be varied further such that the amount of longitudinal motion increases in proportion to the vacuum pressure, while the amount of simultaneous torsional and longitudinal motion decreases in response to vacuum pressure. In addition, the relative percentages of torsional and longitudinal movement can be further controlled such that the ratio of longitudinal movement to torsional movement (or the ratio of longitudinal power to torsional power) is varied. For example, the proportion of simultaneous torsional and longitudinal movement can be varied such that relatively more longitudinal movement (and relatively less torsional movement) is present at the cutting tip.

Figure 4D:
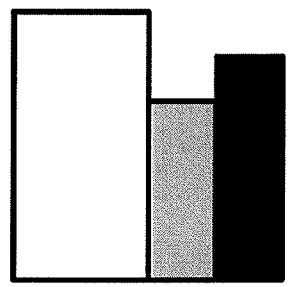

FIG. 4D depicts a power pulse with a first portion that produces torsional movement of the cutting tip, a second portion that produces simultaneous torsional and longitudinal movement of the cutting tip, and a third portion that produces longitudinal motion of the cutting tip. The amplitude and duration of the simultaneous torsional and longitudinal movement of the cutting tip may be proportional to the vacuum pressure. As vacuum pressure increases, the duration of the pulse that produces torsional movement may decrease, while the amplitude and duration of the pulse that produces simultaneous torsional and longitudinal motion may increase in a manner similar to that depicted in plot A of FIG. 3. Likewise, the amplitude and duration of the longitudinal movement of the cutting tip may be proportional to the vacuum pressure. As vacuum pressure increases, the duration of the pulse that produces torsional movement may decrease, while the amplitude and duration of the pulse that produces longitudinal motion may increase in a manner similar to that depicted in plot B of FIG. 3. In another embodiment of the present invention, the portion of the pulse that produces torsional movement of the cutting tip may be decreased as vacuum pressure increases, while the remaining portion of the power pulse may include a first portion that produces simultaneous torsional and longitudinal movement of the cutting tip and a second portion that produces longitudinal movement of the cutting tip. The first and second portions may be varied further such that the amplitude and duration of longitudinal motion increases in proportion to the vacuum pressure, while the amplitude and duration of simultaneous torsional and longitudinal motion decreases in response to vacuum pressure. In addition, the relative percentages of torsional and longitudinal movement can be further controlled such that the ratio of longitudinal movement to torsional movement (or the ratio of longitudinal power to torsional power) is varied. For example, the proportion of simultaneous torsional and longitudinal movement can be varied such that relatively more longitudinal movement (and relatively less torsional movement) is present at the cutting tip.

Figure 4E:
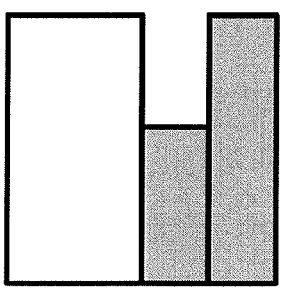

FIG. 4E depicts a power pulse with a first portion that produces torsional movement of the cutting tip and a second portion that produces simultaneous torsional and longitudinal movement of the cutting tip. The duration of the simultaneous torsional and longitudinal movement of the cutting tip may be proportional to the vacuum pressure. As vacuum pressure increases, the duration of the pulse that produces torsional movement may decrease, while the duration of the pulse that produces simultaneous torsional and longitudinal motion may increase in a manner similar to that depicted in plot A of FIG. 3. In addition, the amplitude of the simultaneous torsional and longitudinal movement of the cutting tip may be proportional to the vacuum pressure. As vacuum pressure increases, the duration of the pulse that produces torsional movement may decrease, while the amplitude of the pulse that produces simultaneous torsional and longitudinal motion may increase in a manner similar to that depicted in plot B of FIG. 3. In addition, the relative percentages of torsional and longitudinal movement can be further controlled such that the ratio of longitudinal movement to torsional movement (or the ratio of longitudinal power to torsional power) is varied. For example, the proportion of simultaneous torsional and longitudinal movement can be varied such that relatively more longitudinal movement (and relatively less torsional movement) is present at the cutting tip. In FIG. 4E, the pulse that produces simultaneous torsional and longitudinal movement of the cutting tip is divided into two pulses whose duration and amplitude can be varied in any manner.

Figure 4F:
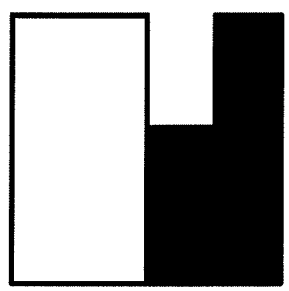

FIG. 4F depicts a power pulse with a first portion that produces torsional movement of the cutting tip and a second portion that produces longitudinal movement of the cutting tip. The duration of the movement of the cutting tip may be proportional to the vacuum pressure. As vacuum pressure increases, the duration of the pulse that produces torsional movement may decrease, while the duration of the pulse that produces longitudinal motion may increase in a manner similar to that depicted in plot A of FIG. 3. In addition, the amplitude of the longitudinal movement of the cutting tip may be proportional to the vacuum pressure. As vacuum pressure increases, the duration of the pulse that produces torsional movement may decrease, while the amplitude of the pulse that produces longitudinal motion may increase in a manner similar to that depicted in plot B of FIG. 3. In FIG. 4E, the pulse that produces simultaneous torsional and longitudinal movement of the cutting tip is divided into two pulses whose duration and amplitude can be varied in any manner.

From the above, it may be appreciated that the present invention provides an improved hand piece for phacoemulsification surgery and an improved controller and method for operating the hand piece. The present invention provides a controller and method of controlling power pulses based on vacuum pressure or vacuum level. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of operating an ophthalmic surgical hand piece, the method comprising:
   providing a series of power pulses to the hand piece, each of the series of power pulses having a first portion that produces torsional movement of a cutting tip and a second portion that produces longitudinal movement of the cutting tip;
   measuring vacuum pressure;
   decreasing the duration of the first portion as vacuum pressure increases; and
   increasing the duration of the second portion as vacuum pressure increases.

2. The method of claim 1 further comprising:
   increasing the amplitude of the second portion as vacuum pressure increases.

3. The method of claim 1 further comprising:
   decreasing the amplitude of the first portion as vacuum pressure increases.

4. A method of operating an ophthalmic surgical hand piece, the method comprising:
   providing a series of power pulses to the hand piece, each of the series of power pulses having a first portion that produces torsional movement of a cutting tip and a second portion that produces simultaneous torsional and longitudinal movement of the cutting tip;
   measuring vacuum pressure;
   decreasing the duration of the first portion as vacuum pressure increases; and
   increasing the duration of the second portion as vacuum pressure increases.

5. The method of claim 4 further comprising:
   increasing the amplitude of the second portion as vacuum pressure increases.

6. The method of claim 4 further comprising:
   decreasing the amplitude of the first portion as vacuum pressure increases.

7. A method of operating an ophthalmic surgical hand piece, the method comprising:
   providing a series of power pulses to the hand piece, each of the series of power pulses having a first portion that produces torsional movement of a cutting tip, a second portion that produces simultaneous torsional and longitudinal movement of the cutting tip, and a third portion that produces longitudinal movement of the cutting tip;
   measuring vacuum pressure;
   altering the duration of the first portion as vacuum pressure increases;
   decreasing the duration of the second portion as vacuum pressure increases; and
   increasing the duration of the third portion as vacuum pressure increases.

8. The method of claim 7 further comprising:
   increasing the amplitude of the second portion as vacuum pressure increases.

9. The method of claim 7 further comprising:
   increasing the amplitude of the third portion as vacuum pressure increases.

10. The method of claim 7 wherein altering the duration of the second portion as vacuum pressure increases further comprises increasing the duration of the second portion as vacuum pressure increases.

* * * * *